US011648537B2

(12) United States Patent
Kuretake et al.

(10) Patent No.: US 11,648,537 B2
(45) Date of Patent: *May 16, 2023

(54) SUPPORTED CATALYST FOR ORGANIC SUBSTANCE DECOMPOSITION AND ORGANIC SUBSTANCE DECOMPOSING APPARATUS

(71) Applicant: Murata Manufacturing Co., Ltd., Nagaokakyo (JP)

(72) Inventors: Satoshi Kuretake, Nagaokakyo (JP); Nario Sugahara, Nagaokakyo (JP); Kentaro Ishihara, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 99 days.

This patent is subject to a terminal disclaimer.

(21) Appl. No.: 17/063,855

(22) Filed: Oct. 6, 2020

(65) Prior Publication Data

US 2021/0016259 A1 Jan. 21, 2021

Related U.S. Application Data

(63) Continuation of application No. PCT/JP2019/008592, filed on Mar. 5, 2019.

(30) Foreign Application Priority Data

May 11, 2018 (JP) .............................. JP2018-092386

(51) Int. Cl.
*B01J 21/04* (2006.01)
*B01J 21/06* (2006.01)
(Continued)

(52) U.S. Cl.
CPC ............. *B01J 23/8892* (2013.01); *A61L 9/03* (2013.01); *B01D 53/865* (2013.01);
(Continued)

(58) Field of Classification Search
CPC ........ B01J 21/04; B01J 21/066; B01J 23/002; B01J 23/34; B01J 23/688; B01J 23/78;
(Continued)

(56) References Cited

U.S. PATENT DOCUMENTS 3,644,147 A * 2/1972 Young, II ................. B01J 35/00
429/528
5,380,692 A * 1/1995 Nakatsuji ............... B01J 23/002
502/313
(Continued)

FOREIGN PATENT DOCUMENTS

EP 2374526 A1 10/2011
JP H0780310 A 3/1995
(Continued)

OTHER PUBLICATIONS

Japanese Office Action issued for Japanese Application No. 2020-518162, date of dispatch Jun. 29, 2021.
(Continued)

*Primary Examiner* — Cam N. Nguyen
(74) *Attorney, Agent, or Firm* — ArentFox Schiff LLP (57) ABSTRACT

A supported catalyst for decomposing an organic substance that includes a carrier and catalyst particles supported on the carrier. The catalyst particles contain a perovskite-type composite oxide represented by $A_xB_yM_zO_w$, where A contains at least one of Ba and Sr, B contains Zr, M is at least one of Mn, Co, Ni, and Fe, y+z=1, x>1, z<0.4, and w is a positive value that satisfies electrical neutrality. An organic substance decomposition rate after the supported catalyst is subjected to a heat treatment at 950° C. for 48 hours is greater than 0.97 when the organic substance decomposition rate before the heat treatment is regarded as 1, and an amount of the catalyst particles peeled off when the supported catalyst is ultrasonicated in water at 28 kHz and 220 W for 15 minutes
(Continued)

is less than 1 wt % of the catalyst particles before untrasonication.

14 Claims, 5 Drawing Sheets

(51) Int. Cl.

| | |
|---|---|
| *B01J 23/00* | (2006.01) |
| *B01J 23/34* | (2006.01) |
| *B01J 23/68* | (2006.01) |
| *B01J 23/78* | (2006.01) |
| *B01J 23/889* | (2006.01) |
| *B01J 35/02* | (2006.01) |
| *B01J 35/04* | (2006.01) |
| *B01J 35/10* | (2006.01) |
| *B01D 53/86* | (2006.01) |
| *B01D 53/94* | (2006.01) |
| *C01G 45/12* | (2006.01) |
| *A61L 9/03* | (2006.01) |
| *C01G 51/00* | (2006.01) |
| *C01G 53/00* | (2006.01) |
| *B01J 37/00* | (2006.01) |
| *B01J 21/16* | (2006.01) |

(52) U.S. Cl.
CPC ..... *B01D 53/8668* (2013.01); *B01D 53/8687* (2013.01); *B01D 53/8696* (2013.01); *B01D 53/94* (2013.01); *B01J 21/04* (2013.01); *B01J 21/066* (2013.01); *B01J 23/002* (2013.01); *B01J 23/34* (2013.01); *B01J 23/688* (2013.01); *B01J 23/78* (2013.01); *B01J 35/026* (2013.01); *B01J 35/04* (2013.01); *B01J 35/1009* (2013.01); *B01J 35/1038* (2013.01); *B01J 35/1061* (2013.01); *B01J 35/1066* (2013.01); *B01J 35/1071* (2013.01); *B01J 35/1076* (2013.01); *C01G 45/125* (2013.01); *C01G 45/1207* (2013.01); *C01G 51/66* (2013.01); *C01G 53/66* (2013.01); *B01D 2255/104* (2013.01); *B01D 2255/2042* (2013.01); *B01D 2255/2047* (2013.01); *B01D 2255/2061* (2013.01); *B01D 2255/2063* (2013.01); *B01D 2255/2073* (2013.01); *B01D 2255/2092* (2013.01); *B01D 2255/2094* (2013.01); *B01D 2255/20707* (2013.01); *B01D 2255/20715* (2013.01); *B01D 2255/20738* (2013.01); *B01D 2255/20746* (2013.01); *B01D 2255/20753* (2013.01); *B01D 2255/20792* (2013.01); *B01D 2255/402* (2013.01); *B01D 2255/9202* (2013.01); *B01D 2255/9207* (2013.01); *B01D 2257/7027* (2013.01); *B01D 2258/01* (2013.01); *B01D 2258/02* (2013.01); *B01J 21/16* (2013.01); *B01J 37/009* (2013.01); *C01P 2002/34* (2013.01); *C01P 2002/50* (2013.01); *C01P 2002/72* (2013.01); *C01P 2002/77* (2013.01); *C01P 2006/12* (2013.01); *C01P 2006/14* (2013.01); *C01P 2006/16* (2013.01)

(58) Field of Classification Search
CPC ...... B01J 23/8892; B01J 35/026; B01J 25/04; B01J 35/1009; B01J 35/1038; B01J 35/1061; B01J 35/1066; B01J 35/1071; B01J 35/1076; B01D 53/865; B01D 53/8668; B01D 53/8687; B01D 53/8696; C01G 45/125; C01G 45/1207; C01G 51/66; C01G 53/66; A61L 9/03

See application file for complete search history.

(56) References Cited

U.S. PATENT DOCUMENTS

| | | | |
|---|---|---|---|
| 6,060,420 A * | 5/2000 | Munakata | B01J 23/002 |
| | | | 502/328 |
| 8,123,931 B2 * | 2/2012 | Kang | C10G 11/20 |
| | | | 585/653 |
| 8,329,612 B2 | 12/2012 | Sato et al. | |
| 8,569,200 B2 * | 10/2013 | Kang | B01J 37/031 |
| | | | 585/653 |
| 2002/0035035 A1 | 3/2002 | Kirchnerova et al. | |
| 2007/0027031 A1 | 2/2007 | Ikeda et al. | |
| 2007/0249497 A1 | 10/2007 | Tanaka et al. | |
| 2009/0108239 A1 | 4/2009 | Caro et al. | |
| 2009/0131252 A1 | 5/2009 | Tanaka et al. | |
| 2009/0286677 A1 | 11/2009 | Takeshima et al. | |
| 2009/0286680 A1 * | 11/2009 | Hirano | B01J 37/0221 |
| | | | 502/326 |
| 2010/0139152 A1 * | 6/2010 | Hucul | C11C 3/10 |
| | | | 44/388 |
| 2012/0074357 A1 | 3/2012 | Sato et al. | |
| 2016/0115835 A1 | 4/2016 | Daido et al. | |

FOREIGN PATENT DOCUMENTS

| | | |
|---|---|---|
| JP | 2000140635 A | 5/2000 |
| JP | 3406001 B2 | 5/2003 |
| JP | 2006231280 A | 9/2006 |
| JP | 2006346603 A | 12/2006 |
| JP | 2006347825 A | 12/2006 |
| JP | 5076377 B2 | 11/2012 |
| JP | 2013244479 A | 12/2013 |
| JP | 2015229137 A | 12/2015 |
| JP | 6036276 B2 | 11/2016 |
| WO | 0016900 A1 | 3/2000 |
| WO | 2004096436 A1 | 11/2004 |
| WO | 2005058490 A1 | 6/2005 |
| WO | 2010143676 A1 | 12/2010 |
| WO | 2014189115 A1 | 11/2014 |
| WO | 2015194451 A1 | 12/2015 |

OTHER PUBLICATIONS

International Search Report issued for PCT/JP2018/045261, dated Feb. 5, 2019.
Kirchenerova, J. et al.; "Design criteria for high-temperature combustion catalysts"; Catalysis Letters, Jul. 2000, vol. 67, No. 2-4, pp. 175-181.
International Search Report issued for PCT/JP2019/017674, dated Jul. 16, 2019.
International Search Report issued for PCT/JP2019/015483, dated Jul. 16, 2019.
International Search Report issued for PCT/JP2019/008592, dated May 21, 2019.
International Search Report issued for PCT/JP2019/008593, dated May 21, 2019.
Written Opinion of the International Searching Authority issued for PCT/JP2019/008593, dated May 21, 2019.
Written Opinion of the International Searching Authority issued for PCT/JP2019/008592, dated May 21, 2019.
Written Opinion of the International Searching Authority issued for PCT/JP2019/015483, dated Jul. 16, 2019.
Written Opinion of the International Searching Authority issued for PCT/JP2019/017674, dated Jul. 16, 2019.
Written Opinion of the International Searching Authority issued for PCT/JP2018/045261, dated Feb. 5, 2019.
Gallucci, Katia et al.; "Catalytic combustion of methane on $BaZr_{(1-x)}Me_xO_3$ perovskites synthesized by a modified citrate method"; Catalysis Today, 2012, vol. 197, No. 1, pp. 236-242.

(56) References Cited

OTHER PUBLICATIONS

Tuyen, Nguyen Van et al.; "Interaction of Hydrogen with Perovskite-supported Metal Catalysts: I. M/$Sr_{1-x}Zr_{1-y}O_{3-x}$ (M=Cu, Pd)"; Kinetics and Catalysis, 1996, vol. 37, No. 4, pp. 575-578.

Yuxi Liu et al.; "Controlled preparation and high catalytic performance of three-dimensionally ordered macroporous LaMnO3 with nanovoid skeletons for the combustion of toluene"; Journal of Catalysis 287, 2012, pp. 149-160.

\* cited by examiner

SUPPORTED CATALYST FOR ORGANIC SUBSTANCE DECOMPOSITION AND ORGANIC SUBSTANCE DECOMPOSING APPARATUS

CROSS REFERENCE TO RELATED APPLICATIONS

The present application is a continuation of International application No. PCT/JP2019/008592, filed Mar. 5, 2019, which claims priority to Japanese Patent Application No. 2018-092386, filed May 11, 2018, the entire contents of each of which are incorporated herein by reference.

FIELD OF THE INVENTION

The present invention relates to a supported catalyst for decomposing an organic substance and an organic substance decomposing apparatus which includes a supported catalyst for decomposing an organic substance.

BACKGROUND OF THE INVENTION

Conventionally, catalysts for decomposing an organic substance have been known.

Patent Document 1 describes a catalyst for decomposing an organic substance which does not contain a noble metal or a rare earth element and is less deteriorated even when being subjected to a heat treatment at 800° C. for 100 hours.

Patent Document 2 describes a catalyst for exhaust gas purification in which a three-way catalyst for exhaust gas purification is supported on a heat resistant carrier.

Patent Document 1: Japanese Patent No. 6303834
Patent Document 2: Japanese Patent No. 3406001

SUMMARY OF THE INVENTION

It has been found that the heat resistance of the catalyst decreases when the catalyst described in Patent Document 1 is supported on a carrier by being mixed with inorganic sol and fired at a low temperature of about 600° C. as in the method described in Patent Document 2. It is considered that this is because the inorganic sol chemically reacts with the catalyst so that the original catalytically active sites do not function and the specific surface area of the catalyst decreases by the sintering promoting action of the inorganic sol.

Meanwhile, it has been found that the adhesion of the catalyst decreases and the peeling rate of the catalyst increases when the catalyst is supported on a carrier without using inorganic sol.

The present invention is intended to solve the above problems, and an object thereof is to provide a supported catalyst for decomposing an organic substance, which can suppress the peeling off of catalyst particles supported on a carrier and its deterioration due to a heat treatment at a high temperature, and an organic substance decomposing apparatus including such a supported catalyst.

The supported catalyst for decomposing an organic substance of the present invention includes a carrier; and catalyst particles supported on the carrier, and in which the catalyst particles contain a perovskite-type composite oxide represented by $A_xB_yM_zO_w$, where the A contains at least one selected from Ba and Sr, the B contains Zr, the M is at least one selected from Mn, Co, Ni, and Fe, y+z=1, x>1, z<0.4, w is a positive value that satisfies electrical neutrality, an organic substance decomposition rate after the supported catalyst is subjected to a heat treatment at 950° C. for 48 hours is greater than 0.97 when the organic substance decomposition rate before the heat treatment is regarded as 1, and an amount of the catalyst particles peeled off when the supported catalyst is ultrasonicated in water at 28 kHz and 220 W for 15 minutes is less than 1 wt % with respect to an initial amount of the catalyst particles before being ultrasonicated.

The x and the z may satisfy $1.001 \leq x \leq 1.05$, and $0.05 \leq z \leq 0.2$.

The x may satisfy $x \geq 1.005$.

A film thickness of a catalyst-supporting film formed of the catalyst particles supported on the carrier may be 5 μm or more.

The carrier may be a porous structure including a plurality of pores having a diameter of 0.3 μm to 50 μm.

The carrier may contain cordierite.

The organic substance decomposing apparatus of the present invention includes the supported catalyst for decomposing an organic substance described above.

According to the supported catalyst for decomposing an organic substance of the present invention, it is possible to suppress the peeling off of the catalyst particles supported on the carrier and suppress the deterioration due to a heat treatment at a high temperature.

The organic substance decomposing apparatus of the present invention provides excellent organic substance decomposition properties since the apparatus includes a supported catalyst for decomposing an organic substance, which can suppress the peeling off of catalyst particles supported on a carrier and its deterioration due to a heat treatment at a high temperature.

DETAILED DESCRIPTION OF THE INVENTION

Hereinafter, the features of the present invention will be specifically described with reference to the embodiments of the present invention.

The supported catalyst for decomposing an organic substance according to the present invention satisfies the following requirements (hereinafter referred to as requirements of the present invention). The supported catalyst for decomposing an organic substance according to the present invention includes a carrier and catalyst particles supported on the carrier, the catalyst particles contain a perovskite-type composite oxide represented by $A_xB_yM_zO_w$, where the A contains at least one selected from Ba and Sr, the B contains Zr, the M is at least one selected from Mn, Co, Ni, and Fe, y+z=1, x>1, z<0.4, w is a positive value that satisfies electrical neutrality, an organic substance decomposition rate after the supported catalyst is subjected to a heat treatment at 950° C. for 48 hours is greater than 0.97 when the organic substance decomposition rate before the heat treatment is regarded as 1, and an amount of the catalyst particles peeled off when the supported catalyst is ultrasonicated in water at 28 kHz and 220 W for 15 minutes is less than 1 wt % with respect to an initial amount of the catalyst particles before being ultrasonicated.

The supported catalyst which satisfies the requirements of the present invention can suppress the peeling off of the catalyst particles supported on the carrier and its deterioration due to a heat treatment at a high temperature as will be described later. This supported catalyst can be used in various applications to decompose organic substances such as purification of exhaust gas from factories and motor vehicles. In that case, it is possible to configure an organic substance decomposing apparatus including a supported catalyst for decomposing an organic substance which satisfies the requirements of the present invention.

Example 1

Powders of high-purity $BaCO_3$, $ZrO_2$, and $MnCO_3$ were weighed so as to have the composition presented in Table 1, pure water was added thereto, and each of the mixtures was wet-mixed together with $ZrO_2$ cobble stones to obtain a slurry. This slurry was dried at 120° C. in a dryer, and the obtained powder was then subjected to a heat treatment at 1100° C. for 2 hours to obtain the intended perovskite-type composite oxide.

Subsequently, in order to obtain a catalyst slurry for supporting, as presented in Table 1, 320 g of pure water was added to 450 g of the perovskite-type compound, appropriate amounts of an organic dispersant and an antifoaming agent were further added thereto, and the mixture was wet-mixed together with $ZrO_2$ cobble stones for 2 hours to obtain a catalyst slurry. Inorganic sol was not used when preparing the catalyst slurry.

A ceramic honeycomb serving as a carrier was immersed in the obtained catalyst slurry for 1 minute. The ceramic honeycomb contains cordierite. In the present embodiment, the ceramic honeycomb is formed of porous cordierite.

Figure 1:
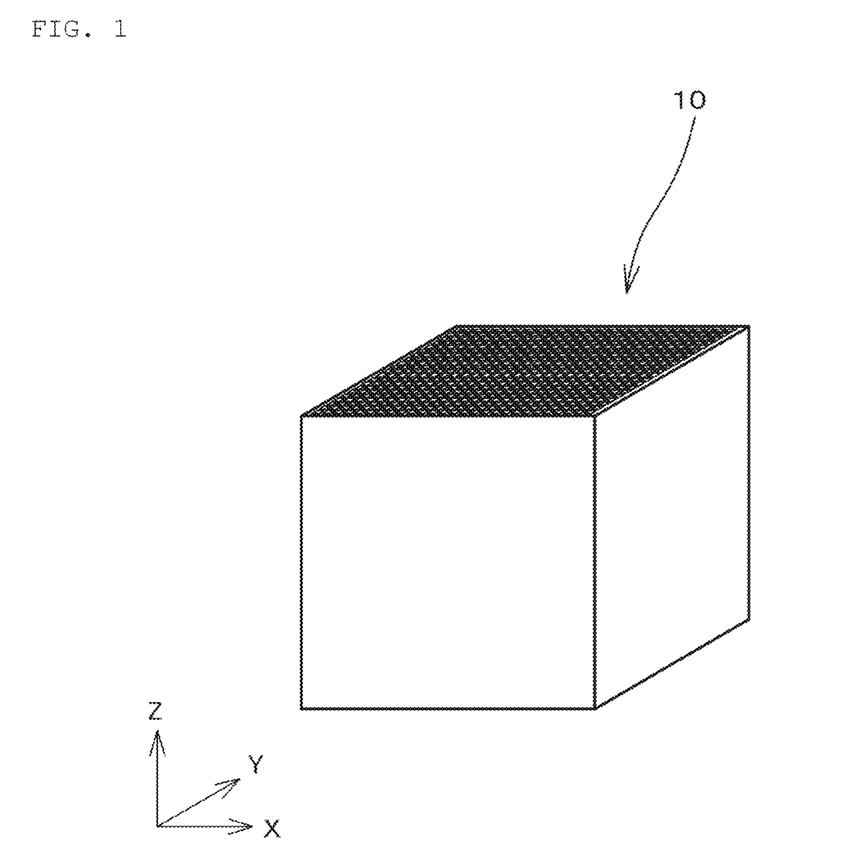
FIG. 1 is a perspective view illustrating an external shape of a ceramic honeycomb.
Figure 2:
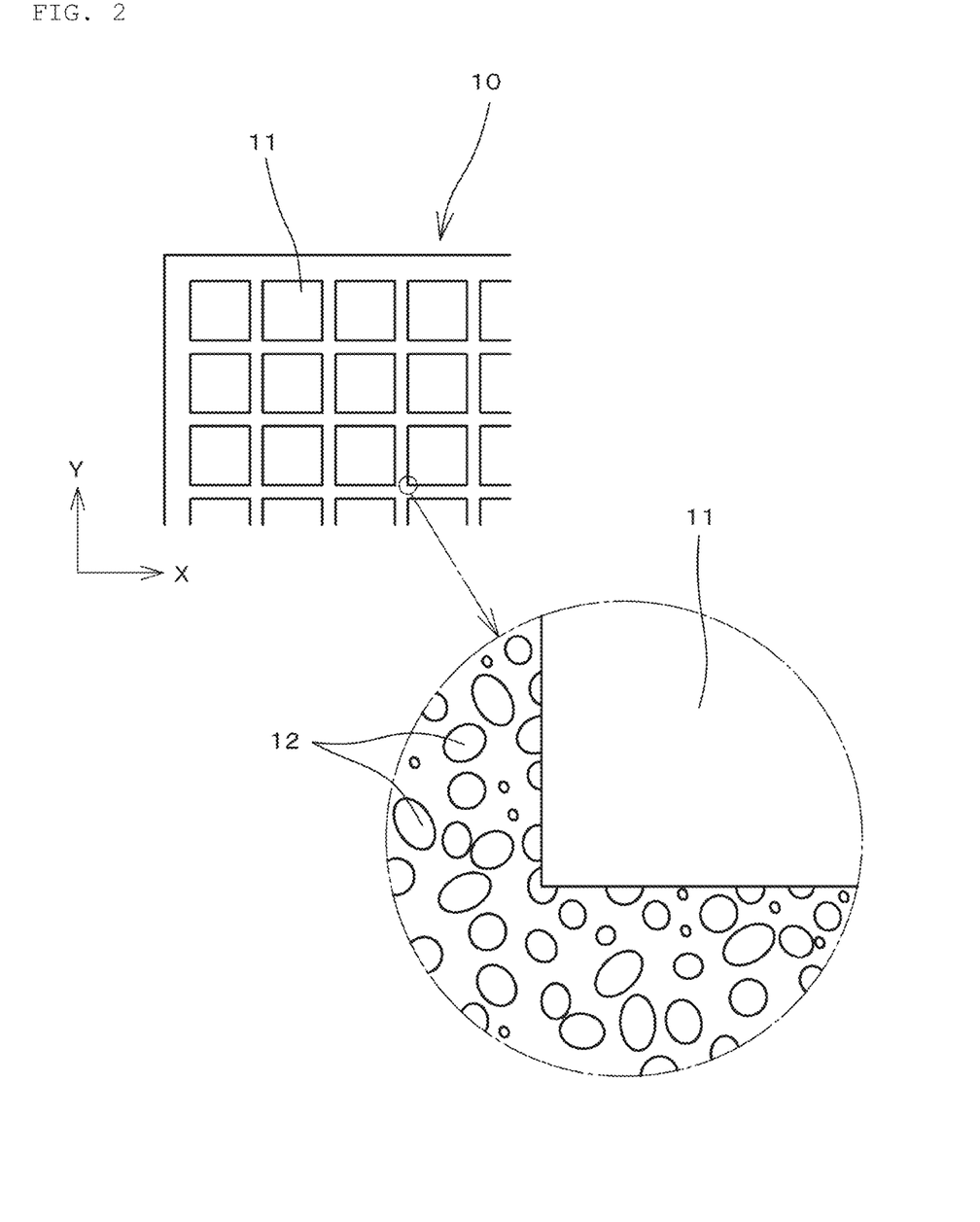
FIG. 2 is an enlarged partial schematic view of the ceramic honeycomb in FIG. 1 when viewed in a Z-axis direction.

FIG. 1 is a perspective view illustrating the external shape of a ceramic honeycomb 10. FIG. 2 is an enlarged partial schematic view of the ceramic honeycomb 10 in FIG. 1 when viewed in the Z-axis direction.

As the size of the ceramic honeycomb 10, the dimension in the X-axis direction in FIG. 1 is about 40 mm, the dimension in the Y-axis direction is about 40 mm, and the dimension in the Z-axis direction is about 50 mm. The ceramic honeycomb 10 is provided with a plurality of cells 11. The size of the cell in the Z-axis direction in a plan view thereof is about 1.5 mm×about 1.5 mm, and the number of cells per 1 $inch^2$ is about 200.

As illustrated in FIG. 2, a great number of pores 12 are provided at the portion other than the cells 11 of the ceramic honeycomb 10. In other words, the ceramic honeycomb 10 is a porous structure including a plurality of pores 12. The pores 12 have a function of allowing the porous cordierite to absorb water contained in the catalyst slurry when the ceramic honeycomb 10 is coated with the catalyst slurry. Therefore, the capillary suction of the pores 12 causes water contained in the catalyst slurry to be absorbed into the porous cordierite and thus increases the concentration of catalyst particles, so that a catalyst supported film in which the catalyst particles adhere to the inner walls of the cells can be formed.

In the present embodiment, the diameter of the pores 12 of the ceramic honeycomb which is the carrier is, for example, 0.3 µm to 50 µm, the average diameter is 3 µm, and the volume porosity is about 50%. The diameter of the pores 12 is an equivalent circle diameter. The diameter and the like of the pores 12 described above are values determined by mercury intrusion porosimetry at a mercury contact angle of 130°, a mercury surface tension of 485 mN/m, and a measurement pressure range of 3.45 kPa to 414 MPa.

In the present invention, the carrier is not limited to the ceramic honeycomb and the diameter, average diameter, and volume porosity of the pores 12 of the carrier are not limited to the above numerical values.

After the immersion of the ceramic honeycomb in the catalyst slurry, the excess catalyst slurry remaining in the ceramic honeycomb was blown off with an air stream, and then the ceramic honeycomb was dried at 120° C. for 12 hours in a dryer. Thereafter, the ceramic honeycomb was fired in the air at a predetermined firing temperature of 500° C. or more and 1150° C. or less (see Table 1) for 3 hours in an electric furnace to obtain a fired product which was a supported catalyst for decomposing an organic substance. In this fired product, catalyst particles are supported on the inner wall of the cells of the ceramic honeycomb which is a carrier.

Figure 3:
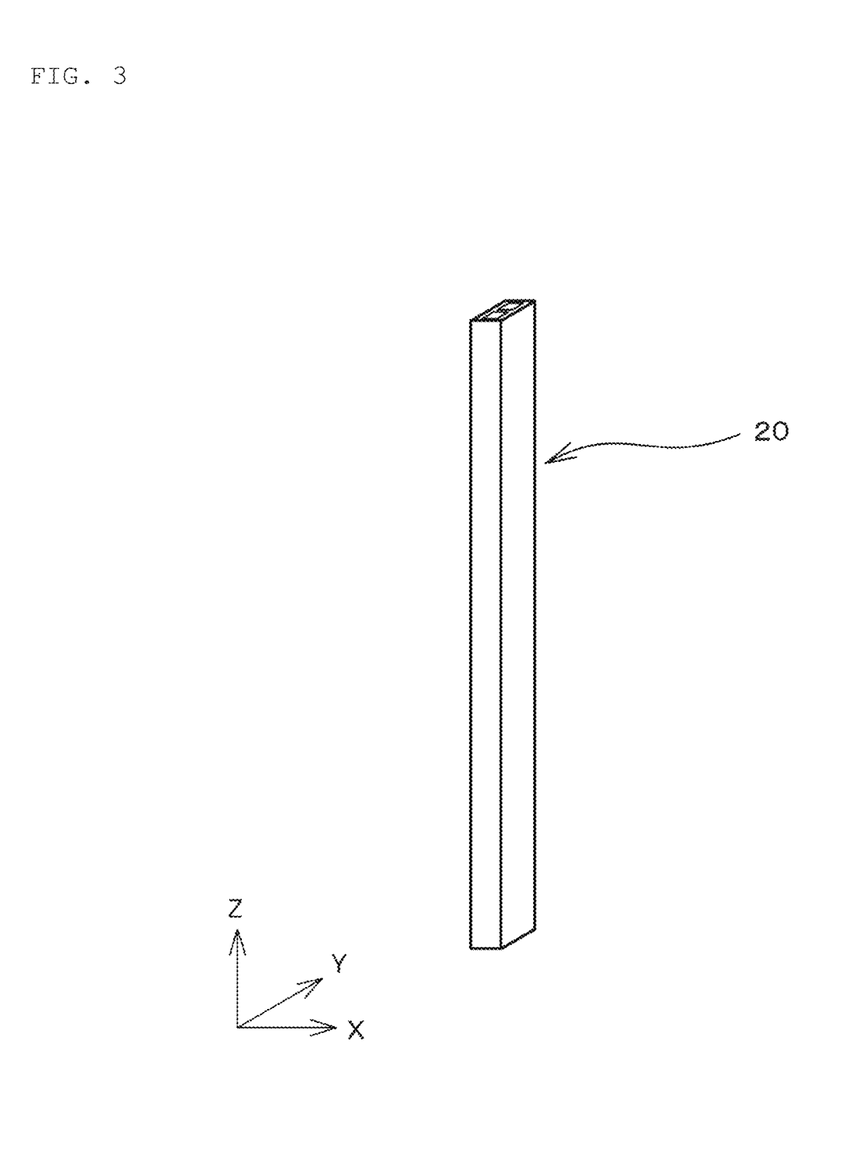
FIG. 3 is a perspective view illustrating an externa shape of a supported honeycomb sample.

Subsequently, the fired product obtained was cut into two-cell sticks, and the excess catalyst attached to the outer peripheral portion was scraped off with sandpaper to obtain a supported honeycomb sample. FIG. 3 is a perspective view illustrating the external shape of a supported honeycomb sample 20. The dimension of the supported honeycomb sample 20 in the X-axis direction is about 2 mm, the dimension thereof in the Y-axis direction is about 4 mm, and the dimension thereof in the Z-axis direction is about 50 mm.

In order to examine the properties of the supported honeycomb sample 20 after being subjected to a heat treatment at a high temperature, some the supported honeycomb samples 20 were subjected to an additional heat treatment at 950° C. for 48 hours in an electric furnace.

By the method described above, supported honeycomb samples for activity evaluation before and after the additional heat treatment were obtained.

<Activity Evaluating Method>

A method for evaluating the activity of the supported honeycomb sample will be described.

(1) Testing Apparatus

Figure 4:
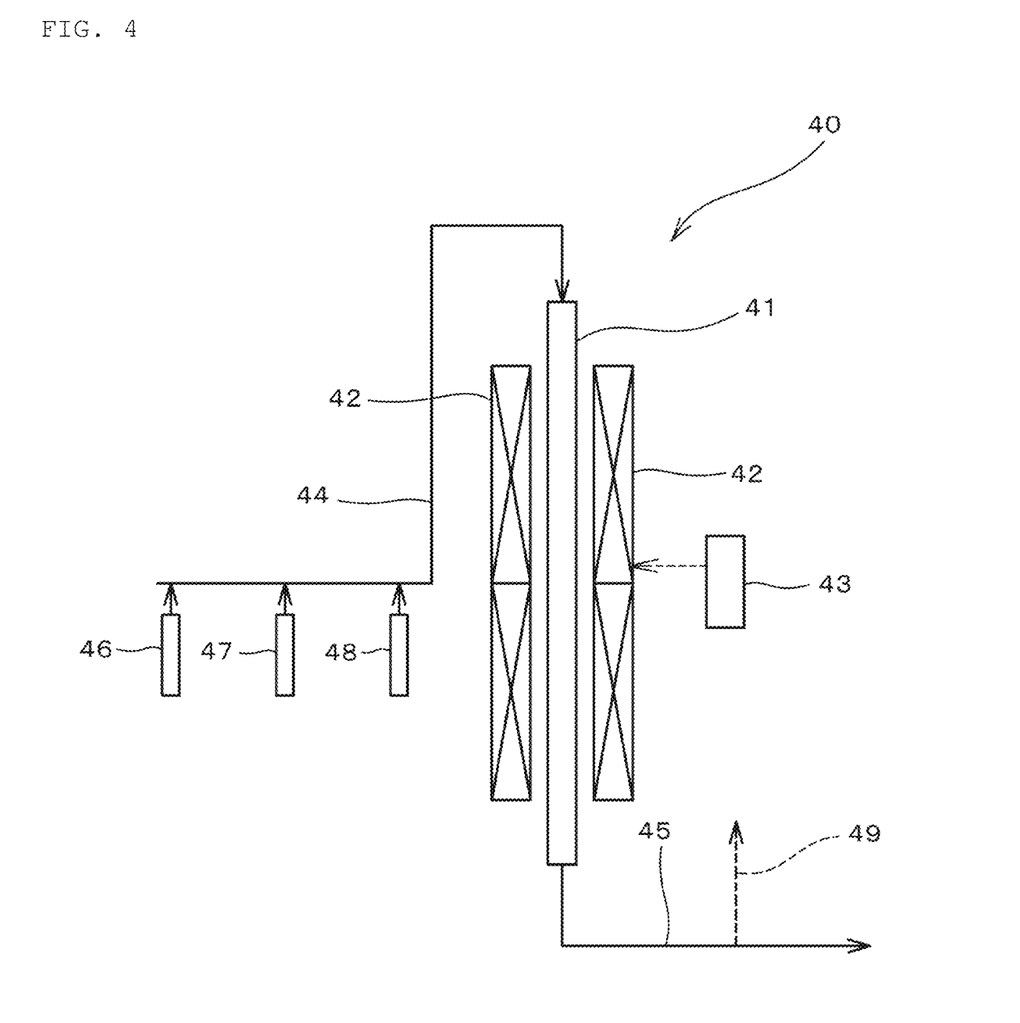
FIG. 4 is a diagram illustrating a schematic configuration of a testing apparatus used for a test to evaluate the organic substance decomposing performance of a supported catalyst for decomposing an organic substance.

FIG. 4 is a diagram illustrating the schematic configuration of a testing apparatus 40 used for a test to evaluate the organic substance decomposing performance of a supported catalyst. This testing apparatus 40 includes a pipe 41 through which an organic substance flows, a heating unit 42 for heating the organic substance flowing through the pipe 41, and a control unit 43 which controls the heating unit 42.

A supported honeycomb sample fabricated by the above-described method is disposed in a region to be heated by the heating unit 42 inside the pipe 41.

Figure 5:
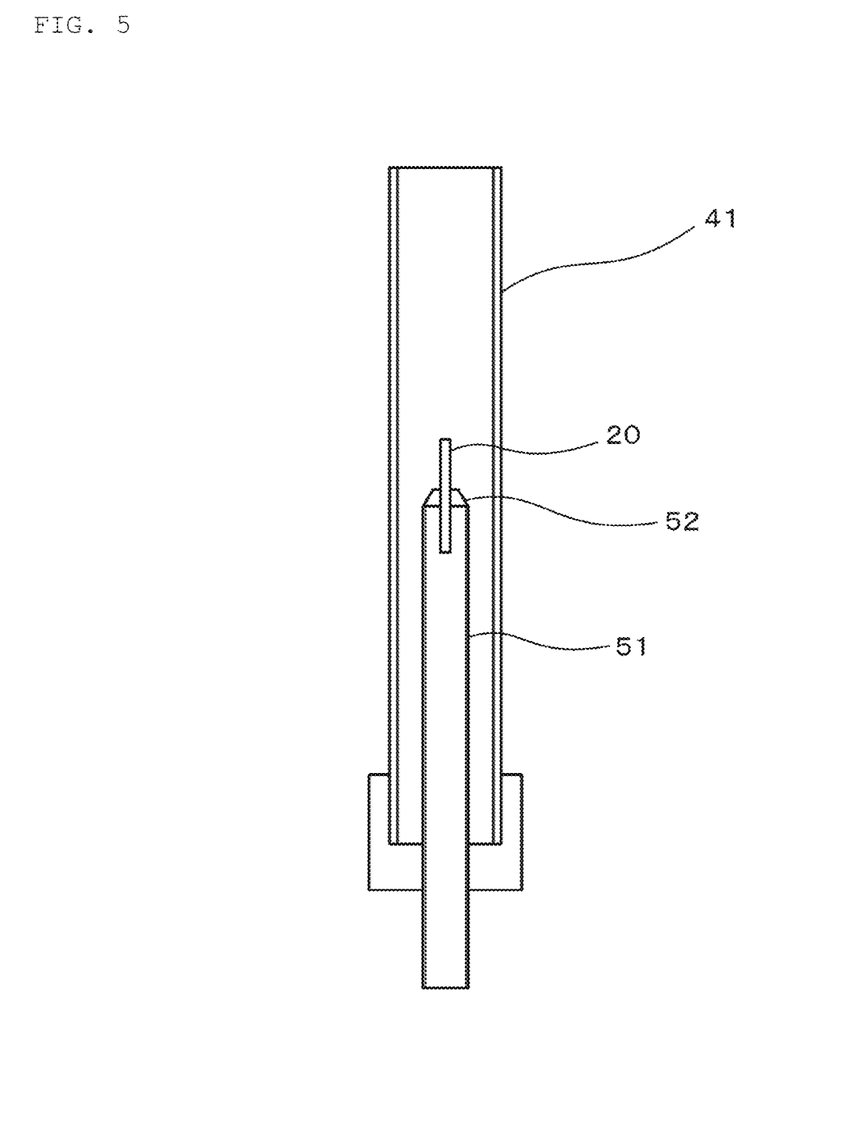
FIG. 5 is a sectional view for explaining a method for disposing a supported honeycomb sample inside a pipe.

FIG. 5 is a sectional view for explaining a method for disposing the supported honeycomb sample 20 inside the pipe 41. The supported honeycomb sample 20 was inserted into a ¼-inch sized reaction pipe 51 up to about half the entire length and fixed and sealed using a heat-resistant inorganic adhesive 52 in that state. Thereafter, the reaction pipe 51 in which the supported honeycomb sample 20 was inserted was inserted into the ½-inch sized pipe 41.

The pipe 41 and the reaction pipe 51 have a double pipe structure, and the gas to be treated which is supplied to the pipe 41 passes through only the interior of the supported honeycomb sample 20 and is discharged to a gas discharge pipe 45 to be described later.

A gas supply pipe 44 is connected on the upstream side of the pipe 41. A toluene supply line 46 for supplying toluene (organic substance), a nitrogen supply line 47 for supplying nitrogen ($N_2$), and an oxygen supply line 48 for supplying oxygen ($O_2$) are connected to the gas supply pipe 44. In other words, the gas to be treated which contains toluene, nitrogen, and oxygen is supplied to the pipe 41 via the gas supply pipe 44.

The gas discharge pipe 45 for discharging the treated gas after being subjected to the decomposition of organic substance in the supported honeycomb sample 20 disposed inside the pipe 41 to the outside of the system is connected on the downstream side of the pipe 41. A sampling line 49 for sampling the treated gas is connected to the gas discharge pipe 45, and the testing apparatus is configured so that the concentration of toluene in the treated gas can be analyzed by gas chromatography.

The control unit 43 is configured so that the temperature of the region heated by the heating unit 42 can be controlled.

(2) Testing Method

Using the testing apparatus 40 described above, a test was conducted in which a gas to be treated which contained toluene, nitrogen, and oxygen was continuously supplied to the pipe 41 and toluene was decomposed. The composition of the gas to be treated was set to toluene ($C_7H_8$): 50 ppm, nitrogen ($N_2$): 80 vol %, and oxygen ($O_2$): 20 vol %, the space velocity SV at the time of measurement was set to 30000 (/h), and the catalyst temperature was set to 400° C.

The treated gas was sampled at the outlet of the sampling line 49, and the toluene concentration was quantified through analysis by gas chromatography. The toluene decomposition rate was determined based on the following Equation (1).

Toluene decomposition rate (%)=100−100×(toluene concentration/50)  (1)

Deterioration rate (%)=100−100×(C2/C1)  (2)

In the above Equation (2), C1 denotes the toluene decomposition rate in the case of using the supported honeycomb sample 20 before the additional heat treatment and C2 denotes the toluene decomposition rate in the case of using the supported honeycomb sample 20 after the additional heat treatment.

Subsequently, a method for evaluating the adhesion of catalyst particles will be described.

First, a fired product, which was a supported catalyst for decomposing an organic substance, was obtained by a similar method to that described above, and then the weight difference between the ceramic honeycomb before supporting of the catalyst and the fired product after supporting of the catalyst is determined to determine the amount W0 of catalyst particles supported.

Next, the fired product is placed in a stainless steel container and immersed in pure water. In this state, the fired product is ultrasonicated at 28 kHz and 220 W for 15 minutes. After that, the fired product is taken out of pure water, thoroughly drained off, and then dried at 120° C. for 12 hours in a dryer. Thereafter, the weight of the fired product after being dried is measured, and the difference between this weight and the weight of the ceramic honeycomb before the catalyst is supported is determined to determine the amount W1 of catalyst particles remaining.

Based on the amount W0 of catalyst particles supported and the amount W1 of catalyst particles remaining that were determined by the methods described above, the peeling rate of catalyst particles was determined according to the following Equation (3).

Peeling rate (%)=100−100×(W1/W0)  (3)

Subsequently, a method for measuring the film thickness of the catalyst-supporting film formed of the catalyst particles s supported on the ceramic honeycomb will be described.

A surface, defined in the Y-axis direction and the Z-axis direction, of a stick-like supported honeycomb sample fabricated by a method similar to that described above is polished with #400 sandpaper by about 1 mm. The supported honeycomb sample after polishing is observed in a direction orthogonal to the polished surface under an optical microscope, and the film thickness of the catalyst supported film attached to the inner walls of the cells is measured using a two-point measurement function. The film thickness was measured at five locations at equal intervals in the Z-axis direction, and the average value thereof was determined.

The properties of the supported catalysts for organic substance decomposition of Sample Nos. 1 to 21 fabricated are presented in Table 1.

TABLE 1

| Sample No. | Catalyst ||||||||||| Catalyst slurry ||||
|---|---|---|---|---|---|---|---|---|---|---|---|---|---|---|---|
| | Charged composition ratio |||| A(x) || B(y) | M(z) ||| Compound | Pure water | Inorganic sol (solid content: wt %) ||
| | x | y | z | y+z | Ba | Sr | Zr | Mn | Co | Ni | Fe | g | g | $SiO_2$ | $Al_2O_3$ |
| 1* | 1.000 | 0.900 | 0.100 | 1.000 | 1.000 | | 1.000 | 1.000 | | | | 450 | 320 | | |
| 2* | 1.000 | 0.900 | 0.100 | 1.000 | 1.000 | | 1.000 | 1.000 | | | | 450 | 320 | | |
| 3* | 1.000 | 0.900 | 0.100 | 1.000 | 1.000 | | 1.000 | 1.000 | | | | 450 | 320 | | |
| 4* | 1.010 | 0.900 | 0.100 | 1.000 | 1.000 | | 1.000 | 1.000 | | | | 450 | 320 | | |
| 5* | 1.010 | 0.900 | 0.100 | 1.000 | 1.000 | | 1.000 | 1.000 | | | | 450 | 320 | | |
| 6 | 1.010 | 0.900 | 0.100 | 1.000 | 1.000 | | 1.000 | 1.000 | | | | 450 | 320 | | |
| 7 | 1.010 | 0.900 | 0.100 | 1.000 | 1.000 | | 1.000 | 1.000 | | | | 450 | 320 | | |
| 8* | 1.010 | 0.900 | 0.100 | 1.000 | 1.000 | | 1.000 | 1.000 | | | | 450 | 320 | | |
| 9* | 0.995 | 0.900 | 0.100 | 1.000 | 1.000 | | 1.000 | 1.000 | | | | 450 | 320 | | |
| 10 | 1.001 | 0.900 | 0.100 | 1.000 | 1.000 | | 1.000 | 1.000 | | | | 450 | 320 | | |
| 11 | 1.005 | 0.900 | 0.100 | 1.000 | 1.000 | | 1.000 | 1.000 | | | | 450 | 320 | | |
| 12 | 1.050 | 0.900 | 0.100 | 1.000 | 1.000 | | 1.000 | 1.000 | | | | 450 | 320 | | |
| 13 | 1.100 | 0.900 | 0.100 | 1.000 | 1.000 | | 1.000 | 1.000 | | | | 450 | 320 | | |

TABLE 1-continued

| | | | | | | | | | |
|---|---|---|---|---|---|---|---|---|---|
| 14 | 1.001 | 0.980 | 0.020 | 1.000 | 1.000 | 1.000 | 1.000 | 450 | 320 |
| 15 | 1.001 | 0.950 | 0.050 | 1.000 | 1.000 | 1.000 | 1.000 | 450 | 320 |
| 16 | 1.001 | 0.800 | 0.200 | 1.000 | 1.000 | 1.000 | 1.000 | 450 | 320 |
| 17* | 1.001 | 0.600 | 0.400 | 1.000 | 1.000 | 1.000 | 1.000 | 450 | 320 |
| 18 | 1.050 | 0.980 | 0.020 | 1.000 | 1.000 | 1.000 | 1.000 | 450 | 320 |
| 19 | 1.050 | 0.950 | 0.050 | 1.000 | 1.000 | 1.000 | 1.000 | 450 | 320 |
| 20 | 1.050 | 0.800 | 0.200 | 1.000 | 1.000 | 1.000 | 1.000 | 450 | 320 |
| 21* | 1.050 | 0.600 | 0.400 | 1.000 | 1.000 | 1.000 | 1.000 | 450 | 320 |

| Sample No. | Inorganic sol (solid content: wt %) $ZrO_2$ | Firing temperature | Before additional heat treatment | | | | After additional heat treatment | |
|---|---|---|---|---|---|---|---|---|
| | | | Amount of catalyst supported | | Decomposition rate % | Peeling rate wt % | Decomposition rate % | Deterioration rate % |
| | | | g/L | Film thickness | | | | |
| 1* | | 500° C. | 201 | 37 | 98.4 | 22 | 94.3 | 4.2 |
| 2* | | 800° C. | 199 | 36 | 98.3 | 10 | 94.6 | 3.8 |
| 3* | | 950° C. | 192 | 34 | 97.7 | <1 | 93.6 | 4.2 |
| 4* | | 500° C. | 191 | 35 | 99.2 | 21 | 99 | 0.2 |
| 5* | | 800° C. | 195 | 34 | 99.1 | 8 | 99 | 0.1 |
| 6 | | 950° C. | 193 | 35 | 99.4 | <1 | 99.4 | 0.0 |
| 7 | | 1050° C. | 200 | 36 | 97.9 | <1 | 97.6 | 0.3 |
| 8* | | 1150° C. | 191 | 38 | 78.4 | <1 | 71.3 | 9.1 |
| 9* | | 950° C. | 201 | 37 | 94.8 | <1 | 87.2 | 8.0 |
| 10 | | 950° C. | 198 | 35 | 98.9 | <1 | 97.6 | 1.3 |
| 11 | | 950° C. | 192 | 35 | 99.2 | <1 | 99 | 0.2 |
| 12 | | 950° C. | 210 | 39 | 98.9 | <1 | 98.9 | 0.0 |
| 13 | | 950° C. | 231 | 44 | 89.5 | <1 | 89.4 | 0.1 |
| 14 | | 950° C. | 204 | 38 | 86.7 | <1 | 85.3 | 1.6 |
| 15 | | 950° C. | 202 | 37 | 97.3 | <1 | 96.1 | 1.2 |
| 16 | | 950° C. | 195 | 35 | 98.9 | <1 | 97.5 | 1.4 |
| 17* | | 950° C. | 162 | 29 | 95.8 | <1 | 90.4 | 5.6 |
| 18 | | 950° C. | 221 | 42 | 89.2 | <1 | 89 | 0.2 |
| 19 | | 950° C. | 209 | 40 | 98.4 | <1 | 98.3 | 0.1 |
| 20 | | 950° C. | 198 | 37 | 99.3 | <1 | 98.6 | 0.7 |
| 21* | | 950° C. | 178 | 33 | 98.8 | <1 | 95.7 | 3.1 |

In Table 1, the composition of catalyst, amounts of perovskite-type compound and pure water used to obtain the catalyst slurry for supporting, firing temperature, amount of catalyst supported, decomposition rate, and peeling rate in the supported catalyst before being subjected to additional heat treatment, decomposition rate of the supported catalyst after being subjected to additional heat treatment, and deterioration rate are presented respectively. Among the amounts of catalyst supported, the numerical value indicated by g/L is the amount attained by normalizing the mass (g) of catalyst particles by the volume (L) of carrier, more specifically, the total volume including the cells of the ceramic honeycomb and the cavities in the cells.

In Table 1, samples in which * is attached to Sample No. are samples which do not satisfy the requirements of the present invention described above and samples in which * is not attached to Sample No. are samples which satisfy the requirements of the present invention described above.

Here, of the requirements of the present invention, the requirement that "the organic substance decomposition rate after the supported catalyst is subjected to a heat treatment at 950° C. for 48 hours is greater than 0.97 when the organic substance decomposition rate before the heat treatment is regarded as 1" is equivalent to the fact that the deterioration rate after the additional heat treatment presented in Table 1 is less than 3.0%. The requirement that "the amount of the catalyst particles peeled off when the supported catalyst is ultrasonicated in water at 28 kHz and 220 W for 15 minutes is less than 1 wt % with respect to the initial amount of the catalyst particles before being ultrasonicated" is equivalent to the fact that the peeling rate before the additional heat treatment presented in Table 1 is less than 1 wt %.

The supported catalysts of Sample Nos. 1 to 3 do not satisfy the requirements of the present invention as the composition x of the perovskite-type composite oxide represented by a general formula $A_xB_yM_zO_w$ is 1.000. The peeling rate was significantly higher than 1 wt % in the supported catalyst of Sample No. 1 fired at a firing temperature of 500° C. and the supported catalyst of Sample No. 2 fired at a firing temperature of 800° C., but the peeling rate was less than 1 wt % in the supported catalyst of Sample No. 3 fired at a firing temperature of 950° C. However, in all the supported catalysts of Sample Nos. 1 to 3, the deterioration rate of the toluene decomposition rate was 3.8% or more after the additional heat treatment at 950° C. for 48 hours, and the deterioration rate after the high temperature heat treatment was great.

The supported catalysts of Sample Nos. 4 to 8 are samples in which the composition x is 1.010 and the firing temperature is changed in a range of 500° C. or more and 1150° C. or less. In the supported catalysts of Sample Nos. 4, 5, and 8 which do not satisfy the requirements of the present invention, the numerical value of the peeling rate or the deterioration rate after the additional heat treatment was poor.

In other words, the peeling rate exceeded 1 wt % as the peeling rate of the supported catalyst of Sample No. 4 fired at a firing temperature of 500° C. was 21 wt % and the peeling rate of the supported catalyst of Sample No. 5 fired at a firing temperature of 800° C. was 8 wt %.

The deterioration rate after the additional heat treatment was as high as 9.1% in the supported catalyst of Sample No. 8 fired at a firing temperature of 1150° C. It is presumed that this is because the firing temperature was too high, i.e., 1150° C., thus the specific surface area of the catalyst decreased, and the catalyst was deteriorated by a chemical reaction with the carrier at the time of firing.

In contrast, in the supported catalysts of Sample Nos. 6 and 7 satisfying the requirements of the present invention, the decomposition rate was 97.9% or more, the peeling rate was less than 1 wt %, and the deterioration rate after the additional heat treatment was less than 0.3%. In other words, in the supported catalysts of Sample Nos. 6 and 7 satisfying the requirements of the present invention, the organic substance decomposition rate is high, peeling off of the catalyst particles supported on the carrier is suppressed, and the deterioration due to a heat treatment at a high temperature is suppressed.

The supported catalysts of Sample Nos. 9 to 13 are samples in which the firing temperature is 950° C. and the composition x is changed in a range of 0.995 or more and 1.100 or less. The peeling rates were all less than 1 wt % in the supported catalysts of Sample Nos. 9 to 13.

In the supported catalyst of Sample No. 9 which had a composition x of 0.995 and did not satisfy the requirements of the present invention, the deterioration rate after the additional heat treatment was as high as 8.0%.

On the other hand, the deterioration rate was 1.3% or less in the supported catalysts of Sample Nos. 10 to 13 satisfying the requirements of the present invention. In other words, in the supported catalysts of Sample Nos. 10 and 13 satisfying the requirements of the present invention, the peeling rate of the catalyst particles is low and the deterioration due to a heat treatment at a high temperature is little.

The supported catalysts of Sample Nos. 14 to 21 are samples in which the firing temperature is 950° C. and the composition x is 1.001 or 1.050, and the composition z is changed in a range of 0.020 or more and 0.400 or less. The peeling rates were all less than 1 wt % in the supported catalysts of Sample Nos. 14 to 21.

In the supported catalysts of Sample Nos. 17 and 21 which had a composition z of 0.400 and did not satisfy the requirements of the present invention, the deterioration rates after the additional heat treatment were as high as 5.6% and 3.1%, respectively.

On the other hand, the deterioration rate was 1.6% or less in the supported catalysts of Sample Nos. 14 to 16 and 18 to 20 satisfying the requirements of the present invention. In other words, in the supported catalysts of Sample Nos. 14 to 16 and 18 to 20 satisfying the requirements of the present invention, the peeling rate of the catalyst particles is low and the deterioration due to a heat treatment at a high temperature is little.

Among the supported catalysts which satisfied the requirements of the present invention, in the supported catalysts of Sample Nos. 6, 7, 10 to 12, 15, 16, 19, and 20 in which the composition x satisfied the relation of $1.001 \leq x \leq 1.05$ and the composition z satisfied the relation of $0.05 \leq z \leq 0.2$, the toluene decomposition rate was 90% or more. On the other hand, among the supported catalysts which satisfied the requirements of the present invention, in the supported catalysts of Sample Nos. 13, 14, and 18 in which at least either of the composition x or the composition z did not satisfy the relation ($1.001 \leq x \leq 1.05$, $0.05 \leq z \leq 0.2$), the toluene decomposition rate was less than 90%.

Hence, in the supported catalyst which satisfies the requirements of the invention, it is preferable that the composition x satisfies the relation of $1.001 \leq x \leq 1.05$ and the composition z satisfies the relation of $0.05 \leq z \leq 0.2$.

Among the supported catalysts which satisfied the requirements of the present invention, in the supported catalysts of Sample Nos. 6, 7, 11 to 13, and 18 to 20 in which the composition x satisfied the relation of $x \geq 1.005$, the deterioration rate after the additional heat treatment was 0.7% or less. On the other hand, among the supported catalysts which satisfied the requirements of the present invention, in the supported catalysts of Sample Nos. 10 and 14 to 16 in which the composition x did not satisfy the relation of $x \geq 1.005$, the deterioration rate after the additional heat treatment was 1.2% or more.

Hence, in the supported catalyst which satisfies the requirements of the present invention, it is preferable that the composition x further satisfies the relation of $x \geq 1.005$.

In order to confirm the properties when inorganic sol generally used as a binder was used, supported catalysts of Sample Nos. 22 to 27 in Table 2 were fabricated. These supported catalysts in which * is attached to Sample No. are samples which do not satisfy the requirements of the present invention.

For the supported catalysts of Sample Nos. 22 and 25, the supported catalysts of Sample Nos. 23 and 26, and the supported catalysts of Sample Nos. 24 and 27 in Table 2, $SiO_2$ sol, $Al_2O_3$ sol, and zirconia sol were respectively used as the inorganic sol to prepare the catalyst slurries for supporting. The $SiO_2$ sol has a solid content of 40 wt %, a pH of 9.0, and an average particle diameter of 20 nm. The $Al_2O_3$ sol has a solid content of 20 wt %, a pH of 8.0, and an average particle diameter of 20 nm. The zirconia sol has a solid content of 40 wt %, a pH of 9.5, and an average particle diameter of 90 nm.

The contents of the inorganic sols in the preparation of the catalyst slurries to be supported are as presented in Table 2. As presented in Table 2, the catalyst compositions of the supported catalysts of Sample Nos. 22 to 24 are the same as the catalyst composition of the supported catalyst of Sample No. 1. The catalyst compositions of the supported catalysts of Sample Nos. 25 to 27 are the same as the catalyst composition of the supported catalyst of Sample No. 4. The respective samples were fabricated and evaluated by similar methods to those for the supported catalysts of Sample Nos. 1 and 4 except that the inorganic sol was used. The firing temperature is a low temperature of 500° C. for all the samples.

TABLE 2

| Sample No. | Catalyst | | | | | | | | | | | | Catalyst slurry | | | |
|---|---|---|---|---|---|---|---|---|---|---|---|---|---|---|---|---|
| | Charged composition ratio | | | | A(x) | | B(y) | | M(z) | | | | Com- pound | Pure water | Inorganic sol (solid content: wt %) | |
| | x | y | z | y + z | Ba | Sr | Zr | Mn | Co | Ni | Fe | | g | g | $SiO_2$ | $Al_2O_3$ |
| 1* | 1.000 | 0.900 | 0.100 | 1.000 | 1.000 | | | 1.000 | 1.000 | | | | 450 | 320 | | |
| 22* | 1.000 | 0.900 | 0.100 | 1.000 | 1.000 | | | 1.000 | 1.000 | | | | 450 | 270 | 3 | |
| 23* | 1.000 | 0.900 | 0.100 | 1.000 | 1.000 | | | 1.000 | 1.000 | | | | 450 | 270 | | 3 |

TABLE 2-continued

| | | | | | | | | | | | |
|---|---|---|---|---|---|---|---|---|---|---|---|
| 24* | 1.000 | 0.900 | 0.100 | 1.000 | 1.000 | 1.000 | 1.000 | | 450 | 300 | |
| 4* | 1.010 | 0.900 | 0.100 | 1.000 | 1.000 | 1.000 | 1.000 | | 450 | 320 | |
| 25* | 1.010 | 0.900 | 0.100 | 1.000 | 1.000 | 1.000 | 1.000 | | 450 | 270 | 3 |
| 26* | 1.010 | 0.900 | 0.100 | 1.000 | 1.000 | 1.000 | 1.000 | | 450 | 270 | | 3 |
| 27* | 1.010 | 0.900 | 0.100 | 1.000 | 1.000 | 1.000 | 1.000 | | 450 | 300 | |

| | Catalyst slurry Inorganic sol (solid content: wt %) $ZrO_2$ | Firing temperature | Before additional heat treatment | | | | After additional heat treatment | |
|---|---|---|---|---|---|---|---|---|
| | | | Amount of catalyst supported | | Decomposition rate % | Peeling rate wt % | Decomposition rate % | Deterioration rate % |
| Sample No. | | | g/L | Film thickness | | | | |
| 1* | | 500° C. | 201 | 37 | 98.4 | 22 | 94.3 | 4.2 |
| 22* | | 500° C. | 193 | 36 | 95.4 | <1 | 80.1 | 16.0 |
| 23* | | 500° C. | 192 | 34 | 94.9 | <1 | 78.2 | 17.6 |
| 24* | 3 | 500° C. | 188 | 33 | 97.2 | <1 | 88.6 | 8.8 |
| 4* | | 500° C. | 191 | 35 | 99.2 | 21 | 99 | 0.2 |
| 25* | | 500° C. | 190 | 34 | 96.5 | <1 | 85.1 | 11.8 |
| 26* | | 500° C. | 192 | 35 | 95.2 | <1 | 84.2 | 11.6 |
| 27* | 3 | 500° C. | 195 | 35 | 97.8 | <1 | 89.9 | 8.1 |

As presented in Table 2, the peeling rate was 22 wt % in the supported catalyst of Sample No. 1 in which the catalyst slurry was prepared without using inorganic sol. In contrast, the peeling rate was less than 1 wt % in the supported catalysts of Sample Nos. 22 to 24 which had the same composition as the supported catalyst of Sample No. 1 and in which the catalyst slurry was prepared using inorganic sol. However, the deterioration rate after the additional heat treatment was as high as 8.8% or more in the supported catalysts of Sample Nos. 22 to 24.

As presented in Table 2, the peeling rate was 21 wt % in the supported catalyst of Sample No. 4 in which the catalyst slurry was prepared without using inorganic sol. In contrast, the peeling rate was less than 1 wt % in the supported catalysts of Sample Nos. 25 to 27 which had the same composition as the supported catalyst of Sample No. 4 and in which the catalyst slurry was prepared using inorganic sol. However, the deterioration rate after the additional heat treatment was as high as 8.1% or more in the supported catalysts of Sample Nos. 25 to 27.

In other words, the deterioration rate of the toluene decomposition rate after the additional heat treatment at 950° C. for 48 hours was 3% or more and the deterioration due to the heat treatment at a high temperature was great when the catalyst slurry was prepared using inorganic sol.

Subsequently, the supported catalysts of Sample Nos. 28 to 32 presented in Table 3 were fabricated for the purpose of confirming the properties when the amount of catalyst supported is changed. The supported catalyst of Sample No. 28 in which * is attached to Sample No. is a sample which does not satisfy the requirements of the present invention and the supported catalysts of Sample Nos. 29 to 32 in which * is not attached to Sample No. are samples which satisfy the requirements of the present invention.

As presented in Table 3, the catalyst compositions of the supported catalysts of Sample Nos. 28 to 32 are the same as the catalyst composition of the supported catalyst of Sample No. 6. The respective samples were fabricated and evaluated by similar methods to those for the supported catalyst of Sample No. 6 except that the amount of the perovskite-type compound mixed when preparing the catalyst slurry for supporting was changed. The firing temperature is 950° C. for all the samples.

TABLE 3

| | Catalyst | | | | | | | | | | | | Catalyst slurry | | | |
|---|---|---|---|---|---|---|---|---|---|---|---|---|---|---|---|---|
| | Charged composition ratio | | | | A(x) | | B(y) | | M(z) | | | | Compound | Pure water | Inorganic sol (solid content: wt %) | |
| Sample No. | x | y | z | y + z | Ba | Sr | Zr | Mn | Co | Ni | Fe | | g | g | $SiO_2$ | $Al_2O_3$ |
| 28* | 1.010 | 0.900 | 0.100 | 1.000 | 1.000 | | 1.000 | 1.000 | | | | | 220 | 320 | | |
| 29 | 1.010 | 0.900 | 0.100 | 1.000 | 1.000 | | 1.000 | 1.000 | | | | | 270 | 320 | | |
| 30 | 1.010 | 0.900 | 0.100 | 1.000 | 1.000 | | 1.000 | 1.000 | | | | | 350 | 320 | | |
| 6 | 1.010 | 0.900 | 0.100 | 1.000 | 1.000 | | 1.000 | 1.000 | | | | | 450 | 320 | | |
| 31 | 1.010 | 0.900 | 0.100 | 1.000 | 1.000 | | 1.000 | 1.000 | | | | | 550 | 320 | | |
| 32 | 1.010 | 0.900 | 0.100 | 1.000 | 1.000 | | 1.000 | 1.000 | | | | | 650 | 320 | | |

TABLE 3-continued

| | Catalyst slurry Inorganic sol (solid content: wt %) $ZrO_2$ | Firing temperature | Before additional heat treatment | | | | After additional heat treatment | |
|---|---|---|---|---|---|---|---|---|
| | | | Amount of catalyst supported | | Decomposition rate % | Peeling rate wt % | Decomposition rate % | Deterioration rate % |
| Sample No. | | | g/L | Film thickness | | | | |
| 28* | | 950° C. | 20 | 1 | 61.2 | <1 | 48.6 | 20.6 |
| 29 | | 950° C. | 45 | 5 | 97.6 | <1 | 97.1 | 0.5 |
| 30 | | 950° C. | 118 | 18 | 98.8 | <1 | 98.7 | 0.1 |
| 6 | | 950° C. | 193 | 35 | 99.4 | <1 | 99.4 | 0.0 |
| 31 | | 950° C. | 326 | 73 | 99.2 | <1 | 99.1 | 0.1 |
| 32 | | 950° C. | 450 | 110 | 99 | <1 | 99 | 0.0 |

As presented in Table 3, the film thickness of the catalyst-supporting film increases in the order of Sample Nos. 28, 29, 30, 6, 31, and 32. The peeling rates were all less than 1 wt % in these supported catalysts.

As presented in Table 3, in the supported catalyst of Sample No. 28 which does not satisfy the requirements of the present invention, the film thickness of the catalyst-supporting film was 1 μm and the deterioration rate after the additional heat treatment was as high as 20.6%.

In contrast, in the supported catalysts of Sample Nos. 6 and 29 to 32 in which the film thickness of the catalyst-supporting film was 5 μm or more and the requirements of the present invention were satisfied, the deterioration rate after the additional heat treatment was 0.5% or less.

In other words, in the supported catalyst in which the film thickness of the catalyst-supporting film is 5 μm or more, the peeling rate is less than 1 wt % and the deterioration rate after an additional heat treatment at 950° C. for 48 hours is less than 3%, more specifically 0.5% or less. Hence, it is preferable that the film thickness of the catalyst-supporting film is 5 μm or more.

Subsequently, the supported catalysts of Sample Nos. 33 to 52 presented in Table 4 were fabricated for the purpose of confirming the properties when the composition of catalyst was changed. Here, in addition to the raw material powders used when fabricating the supported catalysts of Sample Nos. 1 to 21 in Table 1, high-purity $SrCO_3$ powder, $Co_3O_4$ powder, NiO powder, and $Fe_2O_3$ powder were prepared, and perovskite-type composite oxides were fabricated so as to have the compositions presented in Table 4.

In addition, in the course of preparing the catalyst slurry for supporting, the amounts of perovskite-type compound and pure water were changed to the amounts presented in Table 4 depending on the composition. The method for evaluating the supported catalysts for organic substance decomposition fabricated is the same as the evaluation method described above.

TABLE 4

| | Catalyst | | | | | | | | | | | | Catalyst slurry | | | |
|---|---|---|---|---|---|---|---|---|---|---|---|---|---|---|---|---|
| | Charged composition ratio | | | | A(x) | | B(y) | M(z) | | | | | Compound | Pure water | Inorganic sol (solid content: wt %) | |
| Sample No. | x | y | z | y + z | Ba | Sr | Zr | Mn | Co | Ni | Fe | | g | g | $SiO_2$ | $Al_2O_3$ |
| 33* | 1.000 | 0.900 | 0.100 | 1.000 | 1.000 | | 1.000 | | 1.000 | | | | 450 | 320 | | |
| 34 | 1.001 | 0.900 | 0.100 | 1.000 | 1.000 | | 1.000 | | 1.000 | | | | 450 | 320 | | |
| 35 | 1.005 | 0.900 | 0.100 | 1.000 | 1.000 | | 1.000 | | 1.000 | | | | 450 | 320 | | |
| 36 | 1.005 | 0.800 | 0.200 | 1.000 | 1.000 | | 1.000 | | 1.000 | | | | 450 | 320 | | |
| 37* | 1.005 | 0.600 | 0.400 | 1.000 | 1.000 | | 1.000 | | 1.000 | | | | 450 | 320 | | |
| 38* | 1.000 | 0.900 | 0.100 | 1.000 | 1.000 | | 1.000 | 0.400 | 0.400 | 0.100 | 0.100 | | 450 | 320 | | |
| 39 | 1.001 | 0.900 | 0.100 | 1.000 | 1.000 | | 1.000 | 0.400 | 0.400 | 0.100 | 0.100 | | 450 | 320 | | |
| 40 | 1.005 | 0.900 | 0.100 | 1.000 | 1.000 | | 1.000 | 0.400 | 0.400 | 0.100 | 0.100 | | 450 | 320 | | |
| 41 | 1.005 | 0.800 | 0.200 | 1.000 | 1.000 | | 1.000 | 0.400 | 0.400 | 0.100 | 0.100 | | 450 | 320 | | |
| 42* | 1.005 | 0.600 | 0.400 | 1.000 | 1.000 | | 1.000 | 0.400 | 0.400 | 0.100 | 0.100 | | 450 | 320 | | |
| 43* | 1.000 | 0.900 | 0.100 | 1.000 | | 1.000 | 1.000 | | 1.000 | | | | 370 | 320 | | |
| 44 | 1.001 | 0.900 | 0.100 | 1.000 | | 1.000 | 1.000 | | 1.000 | | | | 370 | 320 | | |
| 45 | 1.005 | 0.900 | 0.100 | 1.000 | | 1.000 | 1.000 | | 1.000 | | | | 370 | 320 | | |
| 46 | 1.005 | 0.800 | 0.200 | 1.000 | | 1.000 | 1.000 | | 1.000 | | | | 370 | 320 | | |
| 47* | 1.005 | 0.600 | 0.400 | 1.000 | | 1.000 | 1.000 | | 1.000 | | | | 370 | 320 | | |
| 48* | 1.000 | 0.900 | 0.100 | 1.000 | 0.500 | 0.500 | 1.000 | 0.700 | 0.200 | 0.050 | 0.050 | | 400 | 320 | | |
| 49 | 1.001 | 0.900 | 0.100 | 1.000 | 0.500 | 0.500 | 1.000 | 0.700 | 0.200 | 0.050 | 0.050 | | 400 | 320 | | |
| 50 | 1.005 | 0.900 | 0.100 | 1.000 | 0.500 | 0.500 | 1.000 | 0.700 | 0.200 | 0.050 | 0.050 | | 400 | 320 | | |
| 51 | 1.005 | 0.800 | 0.200 | 1.000 | 0.500 | 0.500 | 1.000 | 0.700 | 0.200 | 0.050 | 0.050 | | 400 | 320 | | |
| 52* | 1.005 | 0.600 | 0.400 | 1.000 | 0.500 | 0.500 | 1.000 | 0.700 | 0.200 | 0.050 | 0.050 | | 400 | 320 | | |

TABLE 4-continued

| | Catalyst slurry Inorganic sol (solid content: wt %) ZrO2 | Firing temperature | Before additional heat treatment | | | | After additional heat treatment | |
|---|---|---|---|---|---|---|---|---|
| | | | Amount of catalyst supported | | Decomposition rate % | Peeling rate wt % | Decomposition rate % | Deterioration rate % |
| Sample No. | | | g/L | Film thickness | | | | |
| 33* | | 950° C. | 188 | 38 | 96.3 | <1 | 93.3 | 3.1 |
| 34 | | 950° C. | 192 | 37 | 96.6 | <1 | 94.9 | 1.8 |
| 35 | | 950° C. | 190 | 37 | 97.1 | <1 | 95.8 | 1.3 |
| 36 | | 950° C. | 190 | 36 | 98.5 | <1 | 96.7 | 1.8 |
| 37* | | 950° C. | 195 | 38 | 96.3 | <1 | 91.4 | 5.1 |
| 38* | | 950° C. | 190 | 33 | 94.6 | <1 | 90.9 | 3.9 |
| 39 | | 950° C. | 185 | 35 | 95.1 | <1 | 93.7 | 1.5 |
| 40 | | 950° C. | 193 | 34 | 95.9 | <1 | 95.2 | 0.7 |
| 41 | | 950° C. | 196 | 34 | 97.1 | <1 | 95.8 | 1.3 |
| 42* | | 950° C. | 189 | 33 | 93.5 | <1 | 89.2 | 4.6 |
| 43* | | 950° C. | 157 | 36 | 90.6 | <1 | 87.5 | 3.4 |
| 44 | | 950° C. | 152 | 39 | 91.1 | <1 | 90 | 1.2 |
| 45 | | 950° C. | 155 | 35 | 92.1 | <1 | 91.4 | 0.8 |
| 46 | | 950° C. | 156 | 38 | 95.5 | <1 | 93.2 | 2.4 |
| 47* | | 950° C. | 158 | 38 | 91.6 | <1 | 85.4 | 6.8 |
| 48* | | 950° C. | 173 | 35 | 94.9 | <1 | 91.7 | 3.4 |
| 49 | | 950° C. | 171 | 38 | 95.4 | <1 | 94.1 | 1.4 |
| 50 | | 950° C. | 169 | 36 | 96.7 | <1 | 95.6 | 1.1 |
| 51 | | 950° C. | 169 | 36 | 98.1 | <1 | 97.2 | 1.2 |
| 52* | | 950° C. | 171 | 36 | 96.1 | <1 | 92 | 4.3 |

In Table 4, the supported catalysts in which * is attached to Sample No. are samples which do not satisfy the requirements of the present invention and the supported catalysts in which * is not attached to Sample No. are samples which satisfy the requirements of the present invention.

As presented in Table 4, in the supported catalysts of Sample Nos. 34 to 36, 39 to 41, 44 to 46, and 49 to 51 satisfying the requirements of the present invention, the peeling rate of the catalyst particles was less than 1 wt % and the deterioration rate after the additional heat treatment was 2.4% or less.

In contrast, in the supported catalysts of Sample Nos. 33, 37, 38, 42, 43, 47, 48, and 52 which did not satisfy the requirements of the present invention, the peeling rate of the catalyst particles was less than 1 wt % but the deterioration rate after the additional heat treatment was 3.1% or more.

As presented in Tables 1 to 4, the supported catalyst which satisfies the requirements of the present invention can suppress the peeling off of the catalyst particles supported on the carrier and its deterioration due to a heat treatment at a high temperature.

The present invention is not limited to the embodiments, and various applications and modifications can be added within the scope of the present invention.

DESCRIPTION OF REFERENCE SYMBOLS

10: Ceramic honeycomb
11: Cell
12: Pore
20: Supported honeycomb sample
40: Testing apparatus
41: Pipe
42: Heating unit
43: Control unit
44: Gas supply pipe
45: Gas discharge pipe
46: Toluene supply line
47: Nitrogen supply line
48: Oxygen supply line
49: Sampling line
51: Reaction pipe

The invention claimed is:
1. A supported catalyst for decomposing an organic substance, the supported catalyst comprising:
a carrier; and
catalyst particles supported on the carrier, wherein
the catalyst particles contain a perovskite-type composite oxide represented by $A_xB_yM_zO_w$, where the A contains at least one selected from Ba and Sr, the B contains Zr, the M is at least one selected from Mn, Co, Ni, and Fe, y+z=1, x>1 and z<0.4, and w is a positive value that satisfies electrical neutrality,
an organic substance decomposition rate of the supported catalyst after a heat treatment at 950° C. for 48 hours is greater than 0.97 when the organic substance decomposition rate before the heat treatment is regarded as 1, and
an amount of the catalyst particles peeled off when the supported catalyst is ultrasonicated in water at 28 kHz and 220 W for 15 minutes is less than 1 wt % with respect to an initial amount of the catalyst particles before being ultrasonicated.

2. The supported catalyst for decomposing an organic substance according to claim 1, wherein $1.001 \leq x \leq 1.05$, and $0.05 \leq z \leq 0.2$.

3. The supported catalyst for decomposing an organic substance according to claim 2, wherein $x \geq 1.005$.

4. The supported catalyst for decomposing an organic substance according to claim 1, wherein $x \geq 1.005$.

5. The supported catalyst for decomposing an organic substance according to claim 1, wherein the catalyst particles are supported on the carrier by a catalyst-supporting film having a film thickness of 5 μm or more.

6. The supported catalyst for decomposing an organic substance according to claim 1, wherein the carrier is a porous structure including a plurality of pores having a diameter of 0.3 μm to 50 μm.

7. The supported catalyst for decomposing an organic substance according to claim 1, wherein the carrier contains cordierite.

8. An organic substance decomposing apparatus comprising a flow path for an organic substance, and the supported catalyst for decomposing an organic substance according to claim 1 within the flow path.

9. The organic substance decomposing apparatus according to claim 8, wherein $1.001 \leq x \leq 1.05$, and $0.05 \leq z \leq 0.2$.

10. The organic substance decomposing apparatus according to claim 9, wherein $x \geq 1.005$.

11. The organic substance decomposing apparatus according to claim 8, wherein $x \geq 1.005$.

12. The organic substance decomposing apparatus according to claim 8, wherein the catalyst particles are supported on the carrier by a catalyst-supporting film having a film thickness of 5 μm or more.

13. The organic substance decomposing apparatus according to claim 8, wherein the carrier is a porous structure including a plurality of pores having a diameter of 0.3 μm to 50 μm.

14. The organic substance decomposing apparatus according to claim 8, wherein the carrier contains cordierite.

\* \* \* \* \*